United States Patent [19]

Moroi et al.

[11] Patent Number: 5,204,087

[45] Date of Patent: Apr. 20, 1993

[54] COMPOSITION FOR FOAMING PREPARATION

[75] Inventors: Masami Moroi, Yachiyo; Kimie Ominato, Higata; Toshio Yokoyama, Tokyo; Akira Iwasa, Yotsukaido, all of Japan

[73] Assignee: SS Pharmaceutical Co., Ltd., Tokyo, Japan

[21] Appl. No.: 806,791

[22] Filed: Dec. 12, 1991

Related U.S. Application Data

[63] Continuation of Ser. No. 569,963, Aug. 20, 1990, abandoned.

[30] Foreign Application Priority Data

Aug. 31, 1989 [JP] Japan .................................. 1-226216
Feb. 2, 1990 [JP] Japan .................................. 2-24008

[51] Int. Cl.$^5$ ........................ A61L 9/04; A61K 33/10; A61K 31/70; A61K 31/715
[52] U.S. Cl. ..................................... 424/44; 424/687; 514/23; 514/53; 514/54; 514/60
[58] Field of Search ................ 424/44, 687; 514/560, 514/574, 23, 53, 54, 60

[56] References Cited

U.S. PATENT DOCUMENTS

| | | | |
|---|---|---|---|
| 3,446,894 | 5/1969 | Magid | 514/474 |
| 4,127,645 | 11/1978 | Witzel et al. | 424/44 |
| 4,203,997 | 5/1980 | Küppers et al. | 514/474 |
| 4,650,669 | 3/1987 | Alexander et al. | 424/44 |
| 4,985,252 | 1/1991 | Jung et al. | 514/777 |

FOREIGN PATENT DOCUMENTS

| | | | |
|---|---|---|---|
| 3160 | of 1872 | United Kingdom | 424/44 |
| 1270781 | 4/1972 | United Kingdom . | |

OTHER PUBLICATIONS

The Merck Index 10 ed. (1983) cit #4852, p. 721.
Saleh, S. I., et al. Expo.-Congr. Int. Technol. Pharm., 3rd (1983) pp. 38–48.

*Primary Examiner*—Frederick E. Waddell
*Assistant Examiner*—Raymond J. Henley, III
*Attorney, Agent, or Firm*—Oblon, Spivak, McClelland, Maier & Neustadt

[57] ABSTRACT

A composition for foaming preparation comprising (a) an organic acid of which the crystal surface is coated with a sugar and (b) a carbonate is disclosed. In the composition, an organic acid is completely shut off from a carbonate by a sugar coating so that the acid does not react with the carbonate over a prolonged storage time. When the composition is put into mouth, the sugar which covers the acid is readily dissolved, allowing the acid and the carbonate to react and to generate carbon oxide gas. An excellent foaming calcium preparation can be produced by using calcium carbonate as the carbonate or by adding other salt of calcium to the composition. Such a calcium preparation gives a good taste and favorable feeling upon administration. It is especially suitable for regular administration of calcium over an extended period of time.

10 Claims, No Drawings

COMPOSITION FOR FOAMING PREPARATION

This application is a continuation of application Ser. No. 07/569,963, filed on Aug. 20, 1990, now abandoned.

BACKGROUND OF THE INVENTION

1. Field of the Invention

This invention relates to a composition for foaming preparation, and, more particularly, to a composition for foaming preparation which is stable during a long-term storage and provides a favorable feeling when administered.

2. Description of the Background Art

Foaming preparations are conventionally prepared by the combination of a carbonate and an organic acid. These preparations are, however, very unstable, generating carbon dioxide gas from the reaction of the carbonate and the organic acid in the presence of a small amount of water.

Conventionally, the preparations have been provided as sealed in specially designed packages so as to shut off the humidity. This method, however, could not effectively prevent a carbonate and an organic acid from reacting and from generating carbon dioxide because of water contained in excipients or the like. The preparation thus very frequently could not give the intended effect when it was used.

Several methods have been proposed in order to solve this problem, including a method of incorporating a moisture absorbent such as sodium sulfate anhydride (Japanese Patent Laid-open No. 44013/1979), a method of incorporating a stabilizer (Japanese Patent Laid-open No. 70610/1984), a method of adding sodium monofumarate having a weak reactivity with the organic acid (Japanese Patent Laid-open No. 26214/1976), and the like. These method, however, have drawbacks such as an insufficient moisture-absorving effect, incompatibility of the added components with medicines for oral administration, and the like. They provided no adequate solution to the problem and thus have not practically been used, except that they were applied to some bath-additive compositions.

In spite of the fact that calcium is an essential nutrient for human, its amount of intake tends to be deficient, especially in pregnant or nursing women and growing children who are in need of a lager dose of calcium, aged people who have only weak calcium absorption capability. These people must constantly take a calcium preparation in order to prevent or cure calcipenia.

Since a calcium preparation must be constantly administered for a long period of time as mentioned above, it is desirable that the preparation can be administered with ease giving a favorable feeling. While inorganic calcium compounds have an advantage of making a dosing amount for a specified calcium intake smaller because of their high calcium content, they give unfavorable feeling to the tongue when administered due to their irritating characteristic and insolubility. On the other hand, although organic calcium compounds give favorable feeling to the tongue, a large amount must be dosed because of their low calcium content. This poses a problem when the preparation must be administered for a long period of time. An attempt has been made of providing a preparation in which both an inorganic and organic calcium compound are used together. Such a preparation does not necessarily gives good results.

A strong need has therefore existed for a foaming preparation which is stable during a prolonged storage and which can be widely applied to medicines for oral administration, foods, cosmetics, and the like. Also, there has been a desire for the development of a calcium preparation giving a good taste and favorable feeling upon administration.

SUMMARY OF THE INVENTION

In view of this situation, the present inventors have conducted extensive studies and found that a foaming preparation composition which is stable during an extended storage time could be obtained by the use of an organic acid of which the crystal surface is coated with a sugar and that, if xylitol is used as an excipient, the foaming calcium preparation could give a good taste and favorable feeling upon administration.

Accordingly, an object of this invention is to provide a composition for a foaming preparation comprising (a) an organic acid of which the crystal surface is coated with a sugar, and a composition for foaming preparation comprising (a) such an organic acid and (b) a carbonate.

Another, more specific object of the present invention is to provide a foaming calcium preparation comprising a salt of calcium, xylitol, an organic acid, and a carbonate, as well as a foaming calcium preparation comprising calcium carbonate, xylitol, and an organic acid.

Other objects, features and advantages of the invention will hereinafter become more readily apparent from the following description.

DETAILED DESCRIPTION OF THE INVENTION AND PREFERRED EMBODIMENTS

Any organic acids which are conventionally used for a foaming preparation can be used for the purpose of the present invention without special limitations. Given as examples of such organic acids are ascorbic acid, succinic acid, tartaric acid, citric acid, malic acid, fumaric acid, and the like. They can be used either independently or as a mixture of two or more of them.

As a sugar with which the surface of these organic acids is to be coated, a monosaccharide, a disaccharide, a sugar alcohol, or a polysaccharide, such as glucose, fructose, lactose, sucrose, mannitol, xylitol, starch, cellulose, or the like, can be used either independently or mixed.

A preferable crystal diameter of the organic acid is usually 850 μm or smaller and a preferable thickness of the sugar to be coated onto the organic acid is 20% or smaller of the crystal size, although they depend on the types of the foaming preparations. The amount of the sugar should be sufficient to cover the crystal surface, for example, 50 to 500% by weight, and particularly 100 to 300% by weight, of the amount of the organic acid.

In order to cover the crystal surface of organic acid, the crystals are first fluidized on a coating pan or a centrifugal coating apparatus with a fluidized bed and the surfaces of crystals are wetted by spraying water, a simple syrup, a polymer solution in alcohol, or the like, following which a sugar are sprayed and attached to the crystal surfaces. This procedure is repeated until a prescribed amount of sugar is coated onto the organic acid crystals.

The foaming preparation composition of the present invention can be prepared by mixing (a) the organic acid of which the crystal surface is coated with a sugar prepared in the above manner and (b) a carbonate. There are no restrictions as to the type of carbonate so long as the same is a carbonate commonly used for foaming preparations. Examples include sodium bicarbonate, potassium carbonate, sodium carbonate, calcium carbonate, ammonium carbonate, magnesium carbonate, and the like.

The foaming preparation composition of the present invention can be made into various forms conventionally used for common foaming agents. Since, different from foaming agents of which the crystal surfaces are coated with a polymer, no delay in the dissolution of the organic acid takes place, desirable forms of the foaming preparation composition of the present invention are chewables, granules, subtilized granules, or powders which can give a pleasant feeling of foam when they are directly put into the mouth.

There are no special limitations as to pharmaceutically active components to be incorporated in the composition for forming preparations of the present invention. A foaming calcium preparation can be obtained, if calcium carbonate is used as component (b), a carbonate, or if component (c), a salt of calcium, is formulated.

Here, as component (c), a salt of calcium, either an inorganic calcium compound, e.g. calcium chloride, calcium hydrogen phosphate, precipitated calcium carbonate, oyster shell, or an organic calcium compound, e.g. calcium gluconate, calcium lactate, calcium aspartate, calcium glycerophosphate, or the like, can be used either independently or mixed.

The amount of component (a), an organic acid, in the foaming calcium preparation of the present invention is 0.5 to 50% by weight, and preferably 1 to 10% by weight. The amount of component (b), a carbonate, in the preparation is 0.5 to 50% by weight, and preferably 1 to 10% by weight. When calcium carbonate is used as component (c), a salt of calcium, there is no need to use any other carbonate as component (b). In this case, a preferable amount of calcium carbonate in the foaming calcium preparation is 5 to 80% by weight, and particularly 30 to 60% by weight.

Although the foaming calcium preparation of the present invention can be prepared into various forms, granules, subtilized granules, tablets, or the like are preferable from the aspect of easiness in administration.

In addition to the above essential components, other nutritious components as well as conventional additives such as excipients, binders, disintegrators, lubricants, and the like may be added to the foaming calcium composition depending on the form into which the composition is prepared. Xylitol, starch, crystalline cellulose, mannitol, lactose, sucrose, sorbitol, dextrin, light anhydrous silicic acid, and the like can be given as examples of the excipient. Among these, xylitol gives an especially favorable feeling when administered so that a preparation suitable for extended calcium intake can be obtained by the use of xylitol as an excipient. The amount of xylitol used in the preparation of the present invention for giving such an effect is 5 to 90% by weight, and preferably 40 to 70% by weight. Xylitol improves the feeling upon administration even of the conventional calcium preparations in which an organic acid is incorporated with no covering of sugar.

Cellulose derivatives, especially hydroxypropyl cellulose, synthetic polymer compound, and the like, are given examples of favorable binders used in the composition of the present invention. Starch, crystalline cellulose, carboxymethyl cellulose calcium, and the like are given as preferable disintegrators. As examples of lubricants which are used when composition is tabletted, talc, strearic acid, magnesium stearate, paraffin, and the like can be given.

In addition to these components, other optional components, including, for example, pharmaceutically active components, fragrance-donatining agents, coloring agents, surface active agents, and the like, may be added as required to the composition of the present invention.

In the foaming preparation composition of the present invention, an organic acid is completely shut off from a carbonate and water so that the two components do not react over a prolonged storage time. In addition, since sugars with which crystals of the organic acid is covered are water-soluble, the composition is free from defects in the conventional foaming preparation, such as delayed dissolution of the organic acid, formation of insoluble substances, decreased foaming capability, and the like.

Furthermore, the foaming calcium preparation to which xylitol is incorporated is easy to administer and gives excellent feeling upon administration because of a favorable stimulation in the mouth due to generation of the foam, improved solubility of calcium owing to generation of carbon dioxide, and a cool, fresh feeling given by xylitol. This type of preparation is especially suitable for regular administration of the medicine over an extended period of time.

Other features of the invention will become apparent in the course of the following description of the exemplary embodiments which are given for illustration of the invention and are not intended to be limiting thereof.

EXAMPLES

Example 1

200 g of tartaric acid (particle size: 127–297 μm) was placed in a centrifugal coating apparatus with a fluidized bed (CF-360-S: trade mark, manufactured by Freunt Industrial Co., Ltd.) and centrifuged at 120 rpm. Water was sprayed at a rate of 5 ml per minute to moisten the crystals. 400 g of lactose (particle size: 10–30 μm) was then gradually charged to cover the surfaces of the crystals of tartaric acid. After drying at 50° C., the product was sieved to obtain 585 g of a composition for foaming preparation which passed through a #30 sieve (JP) but not a #200 sieve (JP).

Example 2

1,000 g of citric acid (particle size: 127–297 μm) was placed in a sugar coating pan which was provided to a sugar film coating apparatus (FM-2: trade mark, manufactured by Freunt Industrial Co., Ltd.) and rotated at 40 rpm. Water was sprayed at a rate of 5 ml per minute to moisten the crystals, following which 1,000 g of sucrose (particle size: 10–30 μm) was gradually charged to cover the crystal surface of citric acid. After drying at 50° C., the product was sieved to obtain 1,980 g of a composition for foaming preparation which passed through a #30 sieve (JP) but not a #200 sieve (JP).

Example 3

Subtilized Granule Calcium Preparation

| Component | (% by weight) |
| --- | --- |
| Precipitated calcium | 30 |

| Component | (% by weight) |
| --- | --- |
| Xylitol | 52 |
| Lactose | 4 |
| Hydroxypropyl cellulose | 2 |
| Composition for foaming preparation of Example 1 | 12 |
| Perfume | Small amount |

Method of Preparation

Precipitated calcium, xylitol, and lactose were mixed, kneaded together with a hydroxypropyl cellulose solution in 15% ethanol and ethanol, and granulated using an extrusion granulator (EXR-60: trade mark, manufactured by Fuji Pauwdal Co., equipped with a 0.45 mm screen). After drying at 50° C., the product was sieved to obtain subtilized granules which passed through a #30 sieve (JP) but not a #200 sieve (JP). The particles were mixed with the composition for foaming preparation of Example 1 and perfume, and filled in stick packages.

Example 4

Antiemetic Chewable Preparation

| Component | (% by weight) |
| --- | --- |
| Meclizine hydrochloride | 6.2 |
| Chlorphenyramine maleate | 0.25 |
| Xylitol | 63.75 |
| D-mannitol | 10.55 |
| Light anhydrous silicic acid | 3 |
| Carboxymethyl cellulose | 1.25 |
| Hydroxypropyl cellulose | 1 |
| Magnesium stearate | 3 |
| Talc | 3 |
| Composition for foaming preparation of Example 2 | 4 |
| Sodium bicarbonate | 4 |
| Perfume | Small amount |

Method of Preparation

Meclizine hydrochloride, chlorphenyramine maleate, xylitol, D-mannitol, light anhydrous silicic acid, and carboxymethyl cellulose were mixed and kneaded together with a hydroxypropyl cellulose solution in 10% ethanol and ethanol. After drying at 50° C., the product was sieved. To a portion which passed through a #20 sieve (JP) were added magnesium stearate, talc, the composition for foaming preparation of Example 2, sodium bicarbonate, and perfume. The mixture was tabletted using a rotary tabletting machine manufactured by Kikusui Co., Ltd. to obtain chewables, each weighing 400 mg and having a diameter of 8 mm.

COMPARATIVE EXAMPLE 1

200 g of tartaric acid (particle size: 127–297 μm) was placed in a centrifugal coating apparatus with a fluidized bed (CF-360-S: trade mark, manufactured by Freunt Industrial Co., Ltd.) and centrifuged at 120 rpm. A 5% ethanol solution of hydroxypropyl cellulose was sprayed at a rate of 5 ml/min while drying at a temperature of 40° C. until hydroxypropyl cellulose in an amount equivalent to 5% by weight of tartaric acid was coated. After drying at 50° C., the product was sieved to obtain 205 g of a composition for foaming preparation which passed through a #30 sieve (JP) but not a #200 sieve (JP). A calcium preparation in the form of subtilized granule was prepared from the composition for foaming preparation in the same manner as in Example 3.

COMPARATIVE EXAMPLE 2

Chewable tablets were prepared from the composition for foaming preparation of Comparative Example 1 in the same manner as in Example 4.

TEST EXAMPLE 1

Stability and delay in foaming were tested on the preparations prepared in Examples 3–4 and Comparative Examples 1–2.

Stability was evaluated by leaving samples which were heat sealed in aluminum foil at 50° C. for 1 month, followed by confirmation of generation of gas. No gas generation was observed in samples from Examples 3–4 and Comparative Example 1, demonstrating good stability of these foaming preparations, whereas the sample from Comparative Examples 2 generated some amount of gas.

Samples from Examples 3 and 4 produced gas immediately after they were put into mouth, whereas samples from Comparative Examples 1 and 2 exhibited delay in generating foam and did not give a distinct foam feeling.

These results are the evidence that the composition for foaming preparation compositions of the present invention have the same or better storage stability than polymer coated preparations and present no interference in the reaction of the organic acid and the carbonate. The composition gives a favorable satisfactory feeling of foam when put into mouth and thus can be easily administered. It is particularly suitable for foaming preparations which are to be administered for a extended period of time.

Example 5

1,500 g of precipitated calcium carbonate, 2,683.2 g of xylitol, 220 g of hydroxypropyl cellulose were homogeneously mixed and kneaded with an addition of ethanol, dried at 50° C., and sieved to obtain a product which passed through a #12 sieve (JP) but not a #42 sieve (JP). The product was subjected to a centrifugal coating apparatus with a fluidized bed together with 192 g of tartaric acid on which 200 g of lactose was coated and 4.8 g of a perfume to produce a granule preparation. The preparation was filled in packages, 1.6 g each, a dose to be administered 3 times a day.

Example 6

1,500 g of precipitated calcium carbonate, 125 g of lysine hydrochloride, 75 g of aminoethyl sulfonate, 10 mg of ergocalciferol, 2,663.2 g of xylitol, 240 g of hydroxypropyl cellulose, and 192 g of tartaric acid were homogeneously mixed and kneaded with an addition of ethanol, dried at 50° C., and sieved to obtain a product which passed through a #30 sieve (JP) but not a #200 sieve (JP). A subtilized granule preparation was obtained by an addition 4.8 g of a perfume to the sieved product. The preparation was filled in packages, 1.6 g each, a dose to be administered 3 times a day.

Example 7

2,576 g of calcium hydrogen phosphate, 1,403.2 g of xylitol, and 240 g of hydroxypropyl cellulose were homogeneously mixed and kneaded with an addition of ethanol, dried at 50° C., and passed through a #20 sieve (JP). Tartaric acid, sodium bicarbonate, and magnesium stearate, in an amount of 192 g each, and 4.8 g of a perfume were added, and the mixture was tabletted using a rotary tabletting machine manufactured by Kikusui Co., Ltd. to obtain chewables, each having a diameter of 15 mm and weighing 1.6 g. One chewable is to be dosed at one time, 3 times a day, and dissolved or crushed in the mouth.

Example 8

1,850 g of calcium hydrogen phosphate, 1,850 g of calcium gulconate, 279.2 g of xylitol, and 240 g of hydroxypropyl cellulose were homogeneously mixed and kneaded with an addition of ethanol, dried at 50° C., and passed through a #20 sieve (JP). Tartaric acid, sodium bicarbonate, and magnesium stearate, 192 g each, and 4.8 g of a perfume were added, and the mixture was tabletted using a rotary tabletting machine manufactured by Kikusui Co., Ltd. to obtain chewables, each having a diameter of 15 mm and weighing 1.6 g. One chewable is to be dosed at one time, 3 times a day, and dissolved or crushed in the mouth.

COMPARATIVE EXAMPLE 3

1,500 g of precipitated calcium carbonate, 3,055.2 g of sucrose, and 240 g of hydroxypropyl cellulose were homogeneously mixed and kneaded with an addition of ethanol, dried at 50° C., and sieved to obtain a product which passed through a #12 sieve (JP) but not a #42 sieve (JP). A granule preparation was obtained by an addition 4.8 g of a perfume to the sieved product.

COMPARATIVE EXAMPLE 4

1,500 g of precipitated calcium carbonate, 125 g of lysine hydrochloride, 75 g of aminoethyl sulfonate, 10 mg of ergocalciferol, 2,855.2 g of D-mannitol, and 240 g of hydroxypropyl cellulose were homogeneously mixed and kneaded with an addition of ethanol, dried at 50° C., and sieved to obtain a product which passed through a #30 sieve (JP) but not a #200 sieve (JP). A subtilized granule preparation was obtained by an addition 4.8 g of a perfume to the sieved product.

COMPARATIVE EXAMPLE 5

2,576 g of calcium hydrogen phosphate, 1,787.2 g of lactose, and 240 g of hydroxypropyl cellulose were homogeneously mixed and kneaded with an addition of ethanol, dried at 50° C., and passed through a #20 sieve (JP). 192 g of magnesium stearate and 4.8 g of a perfume were added, and the mixture was tabletted using a rotary tabletting machine manufactured by Kikusui Co., Ltd. to obtain chewables, each having a diameter of 15 mm and weighing 1.6 g.

COMPARATIVE EXAMPLE 6

1,850 g of calcium hydrogen phosphate, 1,850 g of calcium gulconate, 663.2 g of sucrose, and 240 g of hydroxypropyl cellulose were homogeneously mixed and kneaded with an addition of ethanol, dried at 50° C., and passed through a #20 sieve (JP). 192 g of magnesium stearate and 4.8 g of a perfume were added, and the mixture was tabletted using a rotary tabletting machine manufactured by Kikusui Co., Ltd. to obtain chewables, each having a diameter of 15 mm and weighing 1.6 g.

TEST EXAMPLE 2

The feeling upon administration was evaluated on the preparations prepared in Examples 5-8 and Comparative Examples 3-6 by 6 panelists. All preparations of Examples 5-8 were palatable and imparted a good taste without powdery sensation. On the other hand, calcium preparations of Comparative Examples 3-6 were felt powdery and imparted an unfavorable feeling upon administration.

Obviously, numerous modifications and variations of the present invention are possible in light of the above teachings. It is therefore to be understood that within the scope of the appended claims, the invention may be practiced otherwise than as specifically described herein.

What is claimed is:

1. A foaming preparation composition comprising (a) 0.5 to 50% by weight of crystals of an organic acid of which the crystal surface is coated with a compound selected from the group consisting of monosaccharides, disaccharides, polysaccharides and sugar alcohols and (b) 0.5 to 50% by weight of a carbonate.

2. The foaming preparation composition of claim 1 wherein the compound is selected from the group consisting of glucose, fructose, lactose, sucrose, mannitol, yxlitol and starch.

3. A foaming calcium preparation composition comprising (a) 0.5 to 50% by weight of crystals of an organic acid of which the crystal surface is coated with a compound selected from the group consisting of monosaccharides, disaccharides, polysaccharides and sugar alcohols and (b) 0.5 to 50% by weight of calcium carbonate.

4. The foaming calcium preparation composition of claim 3 wherein the compound is selected from the group consisting of glucose, fructose, lactose, sucrose, mannitol, xylitol and starch.

5. A foaming calcium preparation composition comprising (a) 0.5 to 50% by weight of crystals of an organic acid of which the crystal surface is coated with a compound selected from the group consisting of monosaccharides, disaccharides, polysaccharides and sugar alcohols and (b) 0.5 to 50% by weight of a carbonate, and (c) a salt of calcium.

6. The foaming calcium preparation composition of claim 5 wherein the compound is selected from the group consisting of glucose, fructose, lactose, sucrose, mannitol, xylitol and starch.

7. A foaming calcium preparation composition comprising a salt of calcium, 5 to 90% by weight of xylitol, 0.5 to 50% by weight of crystals of an organic acid of which the crystal surface is coated with a compound selected from the group consisting of monosaccharides, disaccharides, polysaccharides and sugar alcohols, and 0.5 to 50% by weight of a carbonate.

8. The foaming preparation composition of claim 7 wherein the compound is selected from the group consisting of glucose, fructose, lactose, sucrose, mannitol, xylitol and starch.

9. A foaming calcium preparation composition comprising 5 to 80% by weight of calcium carbonate, 0.5 to 50% by weight of crystals of an organic acid of which the crystal surface is coated with a compound selected from the group consisting of monosaccharides, disaccharides, polysaccharides and sugar alcohols.

10. The foaming calcium preparation composition of claim 9 wherein the compound is selected from the group consisting of glucose, fructose, lactose, sucrose, mannitol, xylitol and starch.

* * * * *

UNITED STATES PATENT AND TRADEMARK OFFICE
CERTIFICATE OF CORRECTION

PATENT NO. : 5,204,087
DATED : April 20, 1993
INVENTOR(S) : MOROI et al.

It is certified that error appears in the above-identified patent and that said Letters Patent is hereby corrected as shown below:

Column 8, line 23, delete "yxlitol" and insert therefor --xylitol--.

Signed and Sealed this

Twenty-second Day of February, 1994

Attest:

BRUCE LEHMAN

*Attesting Officer*    *Commissioner of Patents and Trademarks*